United States Patent [19]

Williams et al.

[11] Patent Number: 4,686,980
[45] Date of Patent: Aug. 18, 1987

[54] DISPOSABLE BIPOLAR INSTRUMENT

[75] Inventors: Rodger W. Williams; Larry J. Morgan, both of Nashville, Tenn.

[73] Assignee: Alcon Laboratories, Inc., Fort Worth, Tex.

[21] Appl. No.: 853,150

[22] Filed: Apr. 17, 1986

[51] Int. Cl.⁴ .............................................. A61B 17/39
[52] U.S. Cl. ........................... 128/303.13; 128/303.17; 128/321
[58] Field of Search ....................... 128/303.13, 303.17, 128/321–323, 354, 355; 81/418; D24/27

[56] References Cited

U.S. PATENT DOCUMENTS

| | | | |
|---|---|---|---|
| 1,071,978 | 9/1913 | White | 128/303.13 |
| 3,140,715 | 7/1964 | Whitton, Jr. et al. | 128/321 |
| 3,648,702 | 3/1972 | Bean | 128/321 |
| 3,825,004 | 7/1974 | Durden, III | 128/275.1 |
| 4,041,952 | 8/1977 | Morrison, Jr. et al. | 128/303.17 X |
| 4,202,337 | 5/1980 | Hren et al. | 128/303.14 |
| 4,228,800 | 10/1980 | Degler, Jr. et al. | 128/303.14 |
| 4,461,297 | 7/1984 | Sutter | 128/321 |
| 4,506,669 | 3/1985 | Blake, III | 128/354 X |
| 4,517,974 | 5/1985 | Tanner | 128/303.1 |
| 4,548,207 | 10/1985 | Riemels | 128/303.17 |
| 4,566,183 | 2/1986 | Bloom et al. | 29/825 |
| 4,567,890 | 2/1986 | Ohta et al. | 128/303.13 |

OTHER PUBLICATIONS

Aspen Lobs catalogue, 3-29-1978, four pages: "Electrosurgical Accessories", Bipolar Coagulation Forcepts, (2 pages), and Monopolar Handswitching Forceps.

*Primary Examiner*—Lee S. Cohen
*Attorney, Agent, or Firm*—Holman & Stern

[57] ABSTRACT

A disposable bipolar instrument for ophthalmic surgery has a pair of shell halves carrying electrodes. A collar connects the shell halves together, and electrical conductors supply current to and from the respective electrodes. The shell halves are composed of disposable plastic material, as is the connecting collar and cap which connect the parts and hold the wires in place. Squeezing of the shell halves together is guided by a tongue-and-groove type of joint formed between the shell halves by pairs of upstanding walls, the walls having sloped surfaces in respective facing regions to permit deformation of the shell halves together at one end thereof, so as to permit movement of the electorde tips together to perform cauterization. The deformation of the plastic material causes a progressive resistance, thereby permitting a tactile feedback to the user, so that the instrument can be operated where the field of vision of the user is partially or totally obstructed.

8 Claims, 14 Drawing Figures

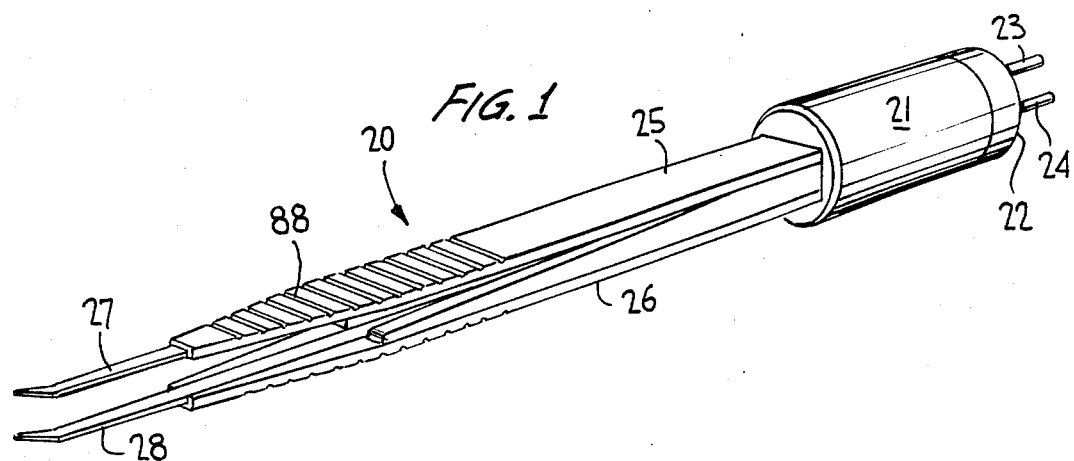
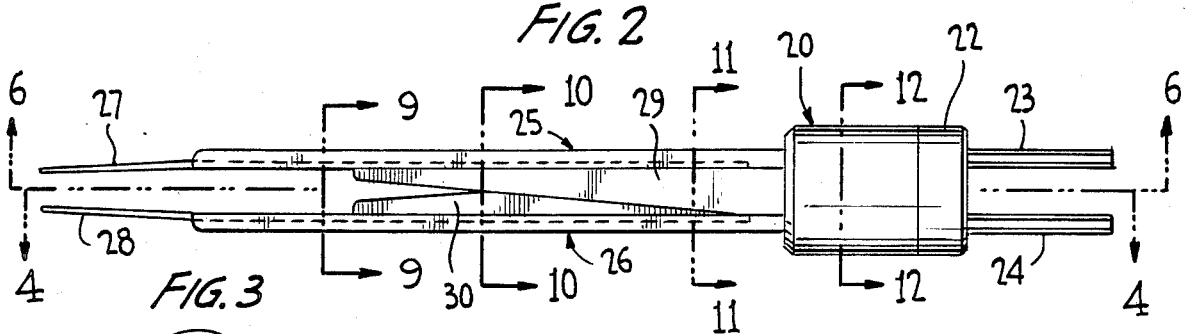
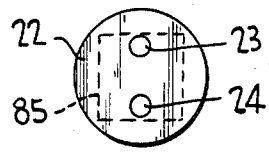
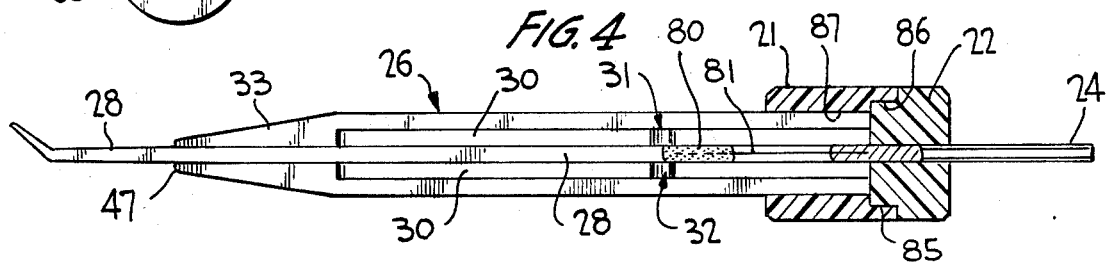
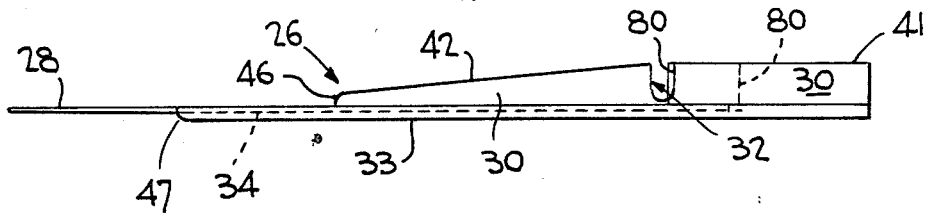

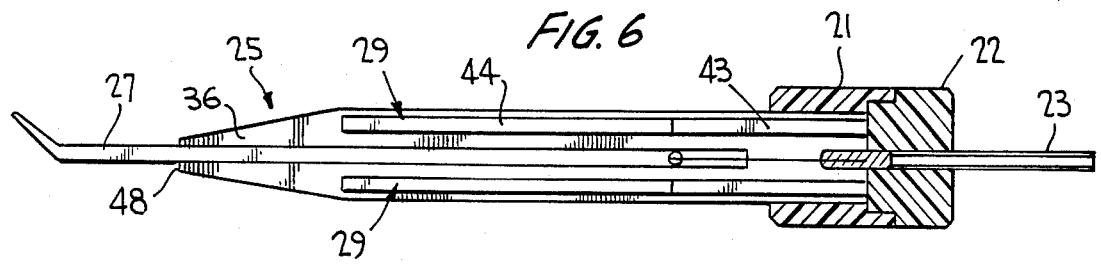
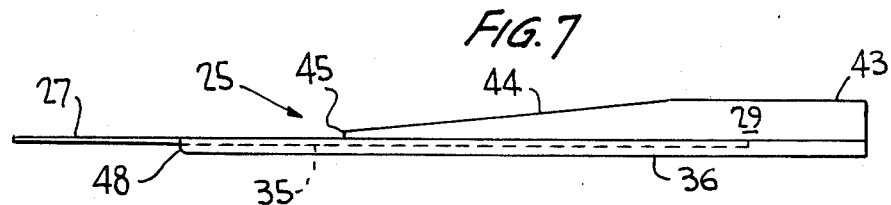
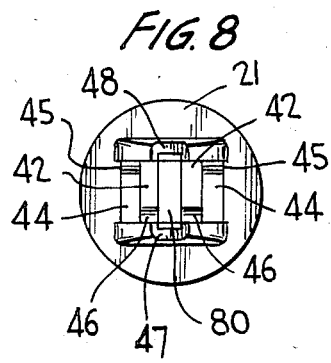 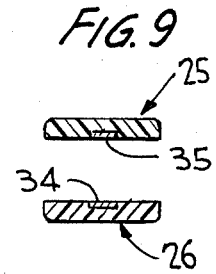 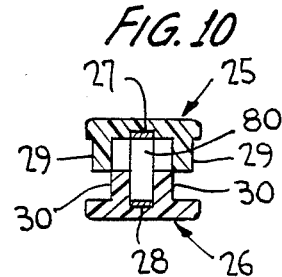 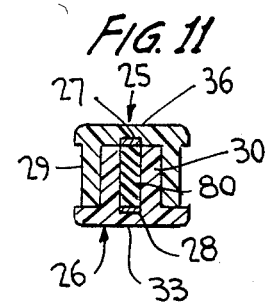
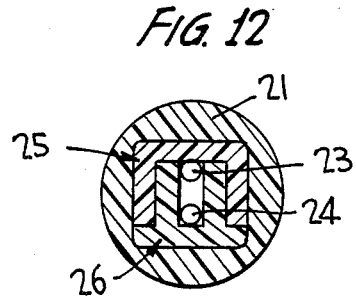 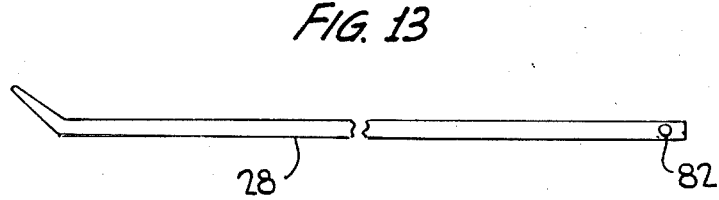
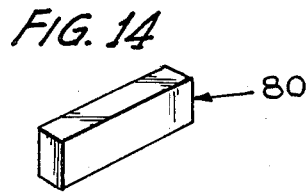

DISPOSABLE BIPOLAR INSTRUMENT

BACKGROUND OF THE INVENTION

The present invention relates to the field of forceps used in cauterizations. In particular, the invention relates to a forceps for cauterization in ophthalmic surgery.

Forceps are known in the prior art generally, and forceps for use in cauterization are also known. Examples of the prior art are discussed hereunder.

In U.S. Pat. No. 4,517,974 to Tanner, a disposable hand-piece is shown. The hand-piece has an internal switching mechanism, and has a cap and body joined to form a conduit for a laser catheter assembly. The cap portion includes a pair of flexible panels which are resilient and biased outwardly so that they can be squeezed by the fingers to turn on an electrical switch which activates the laser beam.

U.S. Pat. No. 3,825,004 to Durden teaches a disposable electrosurgical cautery. U.S. Pat. No. 4,548,207 to Reimels teaches a disposable coagulator having an inner and an outer electrode, formed of plastic with two halves of the shell being adapted to snap together to hold a probe within the housing once it is assembled.

In U.S. Pat. No. 4,228,800 to Degler, Jr. et al, a bipolar microsurgical knife is shown having a center electrode, insulation members, and a non-conducting handle casing. An electrosurgical generator is used to supply electrical power to blade electrodes. A pair of side electrodes are shorted together within the handpiece and act as return electrodes during a cutting operation. A switch controls the type of electrical waveform generated.

In U.S. Pat. No. 4,202,337 to Hren et al, a bipolar knife is shown which is very similar to that discussed hereinabove with respect to U.S. Pat. No. 4,228,800. Here, the structure of the central electrode is shown in detail in two embodiments. A circuit diagram is shown for supplying current to the instrument.

SUMMARY OF THE INVENTION

An object of the present invention is to provide a disposable forceps.

Another object of the present invention is to provide a cauterization forceps for use in ophthalmic surgery.

A further object of the present invention is to provide a forceps for use in ophthalmic surgery which is disposable and which exhibits a progressive resistance to squeezing as a pair of cauterization tips are brought closer together.

A forceps according to the present invention is disposable and has a plastic construction, such that two halves of a plastic shell are attached together fixedly at one end, with each half carrying an electrode. Upon squeezing of the halves together, the shell resiliently deforms to permit the tips of the electrodes to come together. The force required to squeeze the shell halves together is progressive, thereby providing a tactile sense of the closeness of the tips of the forcep arms. This permits the forceps to be used in a situation where the field of vision of the user is partially or totally obstructed.

Upon squeezing of the halves together, the tips of the electrodes come together and permit current to flow between the electrodes at the tips, so as to cauterize any material therebetween. A pair of wires goes to the shell to supply current to one electrode, and to provide a return for a current from the other electrode. Precise registration of the tips is made possible by a tongue-and-groove assembly formed by respective portions of the two shell halves, one shell half having a pair of upstanding walls which snugly receive a pair of upstanding walls fixedly connected to the other one of the shell halves.

The upstanding walls forming the tongue-and-groove are sloped to permit the squeezing together of the shell halves. A separating member is disposed between the shell halves to prevent accidental contact of the electrodes at a location other than the tips as well as to provide a pivot point about which the two shell halves may bend.

BRIEF DESCRIPTION OF THE DRAWINGS

FIG. 1 is a perspective view of a forceps according to the present invention;

FIG. 2 is a top elevational view of the forceps of FIG. 1;

FIG. 3 is a right hand side elevational view of the forceps of FIG. 2;

FIG. 4 is a view taken along line 4—4 of FIG. 2;

FIG. 5 is a side elevational view of a portion of the shell half shown in FIG. 4;

FIG. 6 is a view taken along line 6—6 of FIG. 2;

FIG. 7 is a side elevational view of a portion of the shell half shown in FIG. 6;

FIG. 8 is a left hand elevational view of the forceps of FIG. 2 with the electrodes removed;

FIG. 9 is a sectional view taken along line 9—9 of FIG. 2;

FIG. 10 is a sectional view taken along line 10—10 of FIG. 2;

FIG. 11 is a sectional view taken along line 11—11 of FIG. 2;

FIG. 12 is a sectional view taken along line 12—12 of FIG. 2;

FIG. 13 is a side elevational view of an electrode according to the present invention; and FIG. 14 is a perspective view of a separating member usable in the present invention.

DETAILED DESCRIPTION OF THE INVENTION

FIG. 1 shows a bipolar instrument 20 in perspective view. Shell halves 25 and 26 are connected by a member 21. A cap 22 is connected to the member 21, and supports a pair of wires 23 and 24. Electrodes 27 and 28 project from the free ends of the shell halves 25 and 26. Each of the shell halves has a surface portion 88 adapted for manual gripping as indicated by the lines on the surface of shell half 25 near the exposed portion of the electrode 27.

The term proximal is used to describe the portions of the shell halves 25 and 26, and the portions of the electrodes 27 and 28, which are adjacent or near the member 21, while the term distal is used to describe those portions of the shell halves 25 and 26, and those portions of the electrodes 27 and 28, which are adjacent or near the free ends thereof. The term cantilevered is used to describe the type of structural support given to the distal portions of the shell halves 25 and 26 by the particular construction described hereunder in the region of the member 21 of the instrument 20.

FIG. 2 is a top elevational view of the instrument 20. The shell half 25 has a wall 29 visible in this figure, which partially overlies a wall 30 connected to the shell half 26. The wall 29 is part of "groove" portion of the tongue-and-groove guiding means according to the present invention, for guiding the tips of electrodes 27 and 28 toward one another, so that they are aligned correctly. The wall 30 is part of the "tongue" portion of the tongue and groove guiding means. As seen in this figure, except for the disposition of the walls 29 and 30, the shell halves 25 and 26 are substantially alike.

FIG. 3 is a right hand elevational view of the instrument of FIG. 2. Here, the cap 22 is seen in its true, circular outline. The electrical conductors 23 and 24 pass through the cap 22. In dotted outline is seen the square projection 85 of the cap 22 which projects into a generally square-shaped aperture 86 in the member 21, the aperture 86 in the member 21 being shown in FIGS. 4, 6, and 12.

FIG. 4 is a view taken along line 4—4 of FIG. 2, and shows the shell half 26 and a pair of walls 30,30 in their true view. The cap 22 and the member 21 are in section, and the electrical conductor 24 is shown partially broken away to show the conducting wire 81 which is preferably composed of copper or other conductive metal. A top view of a separating member 80 is seen in FIG. 4.

In the preferred embodiment, the electrode 28 lies within a groove (not shown in FIG. 4; shown in FIG. 5) so that it is generally flush with the surface of the wall 33 of the shell half 26. The pair of upstanding walls 30,30 flank the electrode 28 and are disposed adjacent thereto. A pair of notches 31,32 are formed in generally opposed relationship adjacent one end of the separating member 80 to permit flexure of the shell half 26 about the end of the member 80.

The recess 86 in the member 21 for receiving the projection 85 is indicated in FIG. 4. The shell half 26 is snugly received within an aperture 87 of the member 21, also as indicated in FIG. 4.

The opposed notches 31,32 permit flexure of the upstanding walls 30,30 about the region of the notches, as the walls 30,30 would otherwise tend to prevent flexure of the wall 33 of the shell half 26. The notches 31,32 avoid buckling of the walls 30,30 during flexure by manual operation of the instrument, and in particular avoid buckling of the walls 30,30 during manual deformation of the shell half 26 toward the shell half 25.

As seen in FIG. 4, the separating member 80 overlies an end of the conductor 81, and thus conceals the location of the connection of the conductor 81 to the electrode 28. The connection of the conductor 81 to the electrode 28 can be by any known means, and preferably includes passing of the conductor 81 through an eyelet formed in the electrode 28. Such connection can also be accomplished by soldering, welding, and any other form of electrically connecting the electrode 28 and the conductor 81. The insulation surrounding the conductor 81 is shown partially broken away in FIG. 4.

FIG. 5 shows a side elevational view of the shell portion 26 only of FIG. 4. Here, the shape of the notch 32 is clearly seen, and this notch matches the notch 31 which is therefore not visible in FIG. 5. A projecting end portion of the separating member 80 is seen in FIG. 5. Also, the true shape of each wall 30 is seen in FIG. 5. The walls 30 are preferably shaped identically to one another, and thus only one of the walls 30 is visible in FIG. 5.

The wall 30 seen in FIG. 5 has a sloping portion 42 ending in a tip 46. The wall 30 has a level region 41 which corresponds generally also to the height of the separating member 80. The right hand edge of the member 80 is seen in dotted outline in FIG. 5.

The wall 33 has a groove 34, seen in dotted outline in FIG. 5. The electrode 28 has a thickness which is preferably approximately equal to the depth of the groove 34, so that the electrode 28 is snugly received within the groove 34. The snug fit can be such that, in combination with the presence of the separating member 80, no further connecting means is required for connecting the electrode 28 to the wall 33. If an additional connecting means is desired, such may be used, including, for example, the use of adhesive within the groove 34, the use of a rivet, or the use of any other connecting means suitable for connecting an electrically conductive member to an insulating member such as is formed by the electrode 28 and wall 33, respectively.

The sloped portion 42 of the wall 30 permits room for flexure of the wall 33 about the location of the grooves 31,32 so that upon full closing of the shell half 25 and 26 toward one another, the upper sloped surface 42 of the wall 30 contacts a wall 36 of the shell half 25. This contact is not necessary to the invention, however, and the sloping of the wall 42 may be made greater or lesser in extent, depending upon the degree of flexure of the wall 33 intended to be permitted. According to the present invention, when the electrodes 27 and 28 meet, the walls 29 and 30 forming the tongue-and-groove arrangement prevent misalignment, and therefore contact of the electrode tips of electrodes 27 and 28 also would tend to provide resistance to any further deformation of the shell halves 25 and 26 toward one another. The tips of electrodes 27 and 28 would tend to flex after tip contact is reached, and also during continued deformation of the shell halves 25 and 26 toward one another. Thus, the electrodes 27 and 28, if desired, contribute to the progressive resistance experienced during use, similar to a tweezers or other instrument.

FIG. 6 shows the shell half 25 as seen along line 6—6 of FIG. 2, also showing the member 21 and cap 22 in section. An insulated conductor 23 is seen in FIG. 6 carrying a conductive wire 89, which is similar to the wire 81 of FIG. 4. Voltage is supplied to one of the wires 81 and 89, and the other one of the wires 81 and 89 is grounded so that, as the tips of the electrodes 27 and 28 are brought together, current returns through the remaining one of the wires 81 and 89. Either one of the wires 81 and 89 can serve as the wire connected to a voltage supply (the voltage supply is not shown in the drawings).

FIG. 6 shows the connection of the wire 89 to an eyelet 82 formed in the electrode 27. The upstanding walls 29,29 shown in FIG. 6 are spaced away from the electrode 27, spaced sufficiently to permit a snug reception therebetween of the walls 30,30 of the shell half 26. The shell half 25 has a support wall 36 which supports the electrode 27. The wall 36 has an end 48 as seen in FIG. 6.

FIG. 7 is a side elevational view of the shell half 25 shown in FIG. 6, without the connecting wire 89, the member 21, or cap 22. As seen in FIG. 7, the wall 36 has a groove 35 indicated in dotted outline in FIG. 7. The groove is sufficiently deep in the preferred embodiment to accommodate the thickness of the electrode 27. The width of the groove 35 is just sufficient in the preferred embodiment to receive the electrode 27. The means of connecting the electrode 27 to the wall 36 are similar to that discussed hereinabove with respect to the wall 33 and groove 34 of the shell half 26.

The wall 29 shown in FIG. 7 has a level region 43 and a sloped region 44 which terminates in a tip 45. The height of the wall 29 at the level region 43 in a preferred embodiment corresponds closely to the height of the wall 30 in the level region 41. Thus, when assembled together, the shell halves 25 and 26 are solidly engaged together by the walls 29 and 30, as well as by the respective walls 36 and 33, which in a preferred embodiment are in contact with one another in the region indicated by the level portion 43 and 41. The member 21 serves to retain the shell halves 25 and 26 together in this region. Thus, a solid, tight engagement is formed. It is also contemplated as being within the scope of the present invention to provide any desired additional closing means such as ultrasonic welding, adhesive, glue, screws, or the like, to retain the assembled parts together, even though such is not necessary in the preferred embodiment of the present invention.

The sloped portion 44 corresponds to the sloped portion 42 shown in FIG. 5, so that as the shell halves 25 and 26 are urged toward one another, the sloped portions permit an even, smooth movement until contact with walls 33 and 36. Although no grooves are shown formed in the walls 29,29 such can be provided if desired. The effect of the lack of grooves in wall 29 in the present invention is that the shell half 25 deforms to a lesser extend than does the shell half 26 having the grooves therein. It is contemplated as being within the scope of the present invention to provide grooves in the walls 29,29 to facilitate bending.

FIG. 8 is a left hand elevational view of the instrument shown in FIG. 2, with the electrodes 27 and 28 omitted for clarity. As seen in FIG. 8, the true shape of the grooves 34 and 35 are seen as being generally rectangular. The separating member 80 is also shown in FIG. 8.

The tongue-and-groove relationship of the walls 29 and 30 is seen in FIG. 8, and the snug-fitting relationship of the walls 29 and 30, as well as of the separating member 80 which is disposed between the walls 30,30 is indicated in this figure.

The sectional view shown in FIG. 9 shows a separated portion of the shell halves 25 and 26, and shows the grooves 34 and 35 formed therein. In this figure, as in the previous figure, the electrodes 27 and 28 have been omitted for clarity. This figure has been taken along line 9—9 of FIG. 2.

FIG. 10 is a sectional view of the instrument of FIG. 2 taken along line 10—10 thereof. Here, the sloped portions of the walls 30 and 29 are shown just as they come into contact with one another. The electrodes 27 and 28 are seen in sectional view in this figure.

FIG. 11 is a cross-sectional view of the instrument of FIG. 2 as taken along line 11—11 thereof. Here, the level portions of the walls 29 and 30 are in full engagement with walls 33, 36 respectively of the opposing shell halves, and in full engagement in side-by-side relationship with one another. The separating member 80 is seen in sectional outline in this figure, and the electrodes 27 and 28 are also indicated in section.

FIG. 12 is a sectional view taken along line 12—12 of FIG. 2, and shows the nested structure of the shell halves 25 and 26, as well as the body of the member 21 which retains the shell half 25 and 26 together. A pair of conductors 23 and 24 are seen in section in FIG. 12.

FIG. 13 shows an elevational view of one of the electrodes, electrode 28, showing the eyelet 82 formed to receive a conductive wire. It is contemplated as being within the scope of the present invention that other means of connecting the wire to the electrodes can be used, such as welding, soldering, riveting, and the like.

FIG. 14 is a perspective view of the separating member 80. While a rectangular block is shown, any other separating member can be used having insulating propterties, so as to prevent accidental contact of the conductors 23 and 24, and to prevent accidental contact of the electrodes 27 and 28. For instance, more complex shapes than those shown in FIG. 80 can be used, for example, curved cut-out regions can be provided in the member 80 to accommodate the thickness of the wire and to provide a more snug and sure fit. All such alternative separating means are contemplated as being within the scope of the present invention.

In the foregoing discussion, the preferred embodiment requires no glue or adhesive, or any other adhesive or connecting means, to retain the parts together, other than the assembly of the parts in a tight-fitting relationship. Thus, frictional forces alone are sufficient to retain all of the parts together in the preferred embodiment. This permits economy of manufacture, and the simplified assembly and design permits a high reliability of the finished product against defects. However, any connecting means can be used known to anyone having skill in the fastening, connecting, plastic-working, and metal-working arts to connect any parts of the present invention together, wherever such parts are shown and described as being fixedly connected together herein. The handle body is preferably entirely composed of insulating material, although it is not necessary for the cap 22 to of an insulating material since it is protected from the electrically conductive members 81 and 89 by respective insulating bodies 24 and 23. However, in a preferred embodiment, the cap 22 is also composed of an insulating material, such as of plastics. The plastic used may include any plastic material such as polyethylene, vinyl resins or tis copolymers, modified vinyls, cellulose plastics, polyethylene, polypropylene, or polyolefin resins. Although plastic has been described as the material of choice for the parts of the present invention, except for the electrical conductors, the present invention is not limited thereto, but may include any material which is sufficiently flexible to permit flexing in the regions described, and sufficiently insulating to prevent shorting out of the electrodes. For example, the shell halves 25 and 26 can be formed of wood, if desired, as can the member 21. Additionally, the members 21 and 22 can be formed of a hard ceramic material, rubber, rock, or any other material sufficiently strong to avoid destruction of the parts during use. The material of the member 21 also need not be limited to non-conducting material, and may be composed of metal such as copper, aluminum, steel, or the like, although in the preferred embodiment plastic is used for economy of manufacture.

While a preferred embodiment has been shown and described, the present invention is not limited thereto, but may be otherwise embodied within the scope of the following claims.

What is claimed is:

1. A disposable bipolar instrument for ophthalmic surgery comprising:
   a first shell half having a proximal end and a distal end; a second shell half having a proximal end and a distal end; and a means for connecting said first and said second shell halves at respective proximal ends thereof so that they can function as forceps; said means for connecting including a support portion for maintaining said respective proximal ends in substantially fixed relative relationship, so that said first and second shell halves are cantilevered thereabout; said proximal ends being spaced apart a predetermined distance when no manual force is being applied to said first and second shell halves; said first shell half including a first pair of upstanding wall-like projections; said second shell half including a second pair of upstanding wall-like projections; said first pair of upstanding wall-like projections being in sliding engagement with said second pair of upstanding wall-like projections during manual flexure of said first and second shell halves; said first pair of upstanding wall-like projections being guided, during flexure of said first shell half toward said second shell half, by said second pair of upstanding wall-like projections; said first pair of wall-like projections including a sloped region; and said second pair of wall-like projections including a sloped region; said sloped regions of said first pair of wall-like projections and said second pair of wall-like projections being disposed such that the respective said distal ends of said first and second shell halves can be urged manually toward each other by resilient bending flexure of said first and second shell halves in cantilevered bending; said resilient bending flexure causing a progressive increase in resistive force to further flexure, thereby providing tactile feedback to an operator during manual operation of said first and second shell halves;

a first electrode carried by said first shell half; a second electrode carried by said second shell half;

a connector means for connecting said first and second electrodes to a voltage source; said first and second electrodes projecting beyond said respective distal ends for simultaneous use as forcep tips and as operational electrodes during ophthalmic surgery;

whereby said first electrode and said second electrode can be guided toward and away from one another by manual urging of said first and second shell halves.

2. A disposable bipolar instrument as claimed in claim 1, wherein said first shell half and second shell half are composed of a resiliently deformable plastic material.

3. A disposable bipolar instrument as claimed in the claim 1, wherein said means for connecting said first shell half and said second shell half comprises a collar which snugly receives said respective proximal ends of said first and second shell halves.

4. A disposable bipolar instrument as claimed in claim 3, wherein said respective proximal ends of said first shell half and said second shell half are disposed in mating relationship with each other within said collar.

5. A disposable bipolar instrument as claimed in claim 1, wherein said first shell half has a groove disposed therein which receives said first electrode; and said second shell half has a groove disposed therein which receives said second electrode.

6. A disposable bipolar instrument as claimed in claim 1, further comprising means for maintaining separation of respective proximal ends of said first electrode and said second electrode.

7. A disposable bipolar instrument as claimed in claim 6, wherein said means for maintaining separation comprises a solid insulating body disposed between said first pair of wall like projections of said first shell half adjacent said proximal end thereof.

8. An instrument for ophthalmic surgery, comprising:
a first shell half and a second shell half; said first and second shell halves each having a proximal end and a distal end; said first shell half being resiliently deformable and having a first wall-like projection which supports a second wall-like projection and a third wall-like projection; said second and third wall-like projections being disposed generally perpendicularly to said first wall-like projection; said second wall-like projection and said third wall-like projection being spaced apart and generally parallel to each other; said second shell half being resiliently deformable and having a fourth wall-like projection which supports a fifth wall-like projection and a sixth wall-like projection, said fifth wall-like projection and said sixth wall-like projection being disposed generally perpendicularly to said fourth wall-like projection; said fifth wall-like projection and said sixth wall-like projection being spaced apart and generally parallel to each other;

said first shell half carrying a first electrode; said second shell half carrying a second electrode; said first and second electrodes each having a distal end which projects beyond distal ends of said first and second shell halves;

a first conductor connected to said first electrode for supplying current to said first electrode, and a second conductor connected to said second electrode for carrying current away from said second electrode;

a means for connecting said first shell half to said second shell half at said proximal ends thereof, so that said first and second shell halves can function as forceps; said means for connecting including a portion for maintaining said respective proximal ends in substantially fixed relative relationship, so that said first and second shell halves are cantilevered thereabout; said proximal ends being spaced apart a predetermined distance when no manual force is being applied to said first and second shell halves;

during manual actuation of said first and second shell halves, said second wall-like projection being in sliding engagement with said fifth wall-like projection, and said third wall-like projection being in sliding engagement with said sixth wall-like projection;

whereby manual engagement of said first shell half and said second shell half causes resilient flexural deformation of said first and second shell halves toward one another with a progressive resistance, so as to bring the exposed tips of said first electrode and said second electrode together; whereby cauterization can be performed.

* * * * *